US005439456A

United States Patent [19]
Fabricant

[11] Patent Number: 5,439,456
[45] Date of Patent: Aug. 8, 1995

[54] FASTENING SYSTEM FOR BODY FLUID COLLECTION CONTAINERS

[76] Inventor: Albert Fabricant, 2970 N. Lake Shore Dr., Chicago, Ill. 60657

[21] Appl. No.: 76,083

[22] Filed: Jun. 14, 1993

Related U.S. Application Data

[63] Continuation of Ser. No. 853,784, Mar. 19, 1992, Pat. No. 5,267,987.

[51] Int. Cl.⁶ .............................................. A61M 1/00
[52] U.S. Cl. ............................ 604/327; 128/DIG. 15; 128/DIG. 24
[58] Field of Search ....... 128/760, 767, 761, DIG. 15, 128/DIG. 24; 604/327, 317, 318, 322, 345, 346, 349, 351, 353, 179; 224/191, 222, 252, 148; 4/144.3, 144.2

[56] References Cited

U.S. PATENT DOCUMENTS

| | | | |
|---|---|---|---|
| 3,160,158 | 12/1964 | Rayhart | 604/179 |
| 3,161,199 | 12/1964 | Shaw et al. | 604/179 |
| 3,357,430 | 12/1967 | Rosenberg | 604/353 |
| 4,073,295 | 2/1978 | Laufbahn | 604/353 |
| 4,122,851 | 10/1978 | Grossner | 128/295 |
| 4,215,687 | 8/1980 | Shaw | 128/169 |
| 4,500,019 | 2/1985 | Curley, Jr. | 224/222 |
| 4,511,358 | 4/1985 | Johnson, Jr. et al. | 604/327 |
| 4,624,244 | 11/1986 | Taheri | 128/24 R |
| 4,671,787 | 6/1987 | Widman | 604/179 |
| 4,848,624 | 7/1989 | Clem | 224/222 |
| 4,892,527 | 1/1990 | Zivny | 604/353 |
| 4,901,375 | 2/1990 | Dahlgren | 4/144.3 |
| 4,957,231 | 9/1990 | Kalisher | 224/151 |
| 5,026,362 | 6/1991 | Willett | 604/345 |
| 5,045,979 | 9/1991 | Stevens | 362/108 |
| 5,053,027 | 10/1991 | Manfredi | 604/327 |
| 5,240,156 | 8/1993 | Sicotte et al. | 224/151 |
| 5,267,987 | 12/1993 | Fabricant | 604/327 |

FOREIGN PATENT DOCUMENTS

| | | | |
|---|---|---|---|
| 40611 | of 1906 | United Kingdom | 604/353 |
| 2153231 | 8/1985 | United Kingdom | |

Primary Examiner—Stephen C. Pellegrino
Assistant Examiner—Guy V. Tucker
Attorney, Agent, or Firm—Patula & Associates

[57] ABSTRACT

A system for fastening a body fluid container to a human leg. The device is a band of appropriate shape and length which encircles the human leg. Each end of the band has fasteners, possibly hook and loop fasteners, which coact with each other so that when the ends are fastened, the invention is frictionally supported on the user's thigh. The body fluid container is then attached to the band by the user, by means of fasteners which are also possibly hook and loop fasteners.

6 Claims, 2 Drawing Sheets

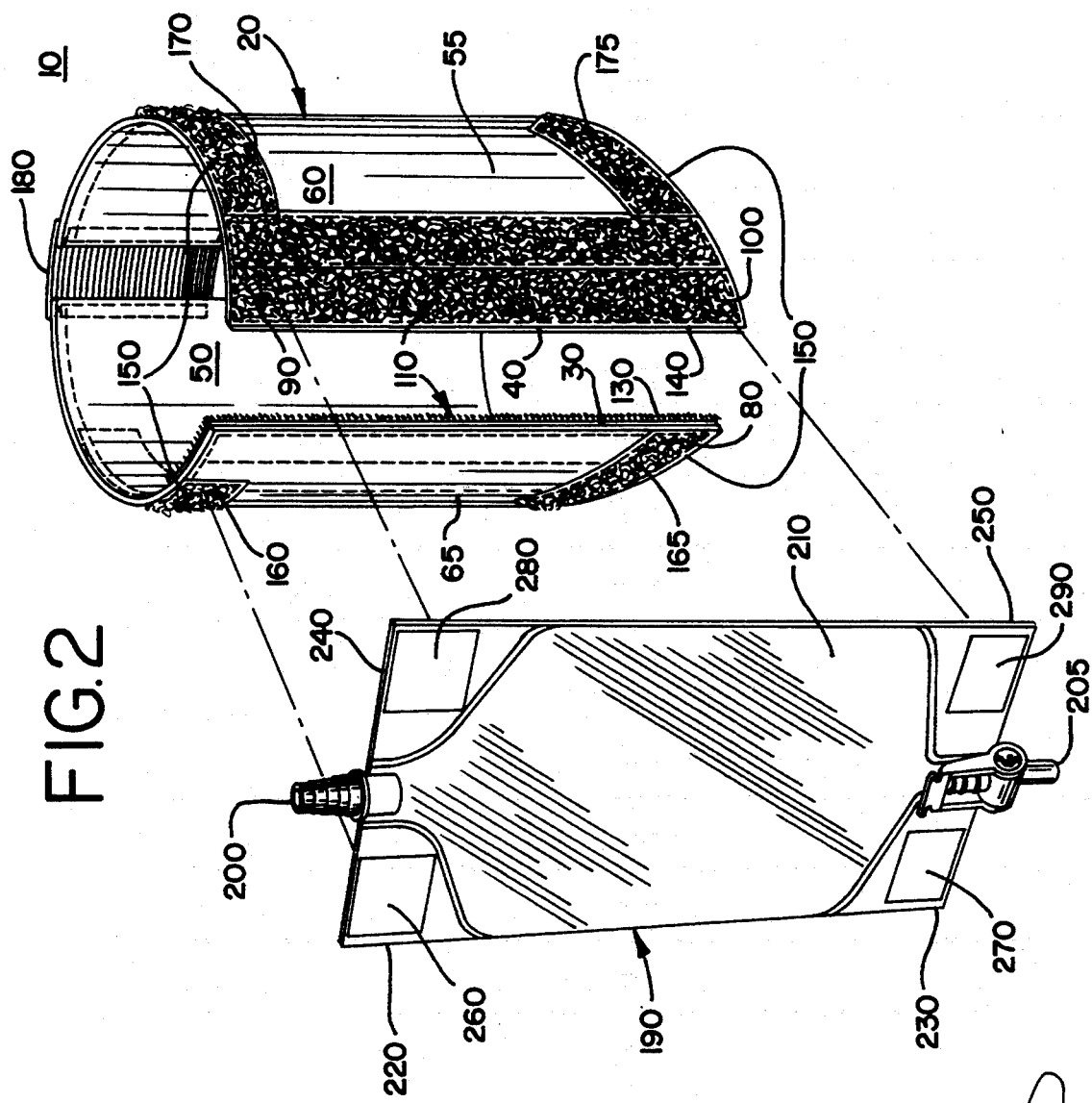

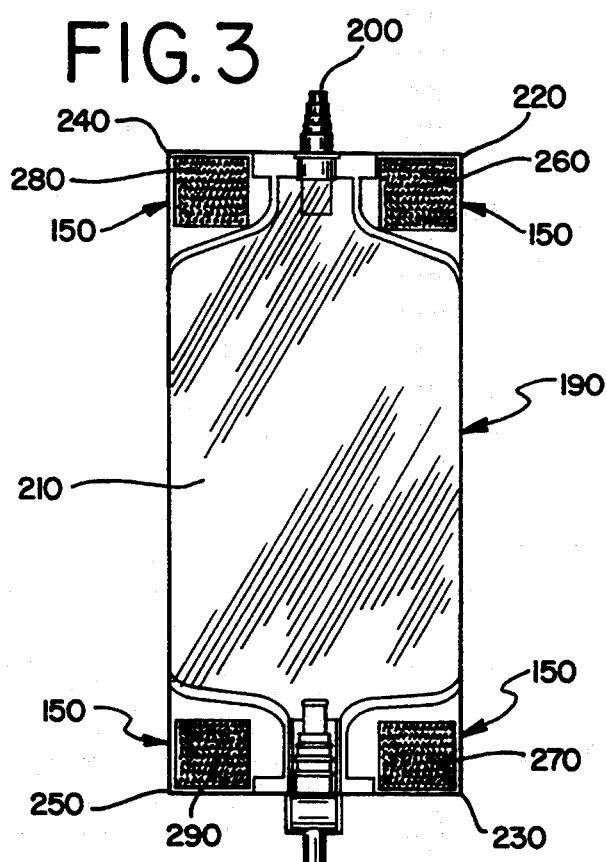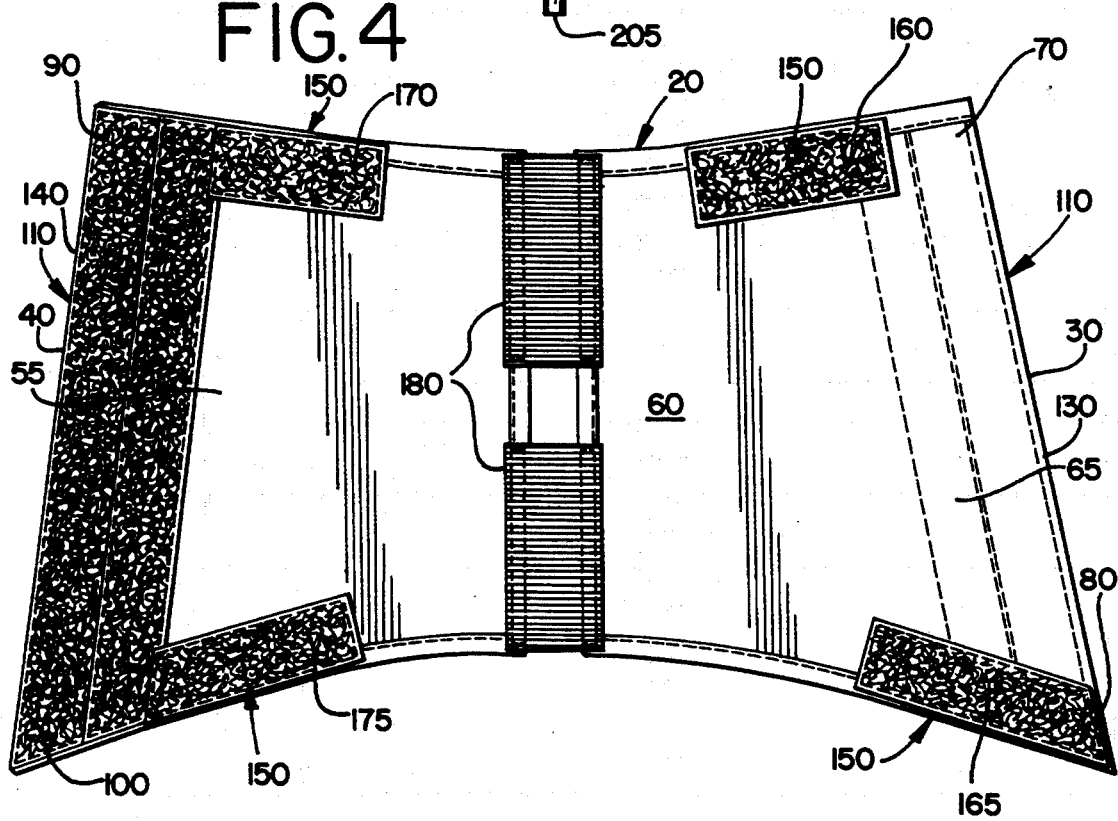

FASTENING SYSTEM FOR BODY FLUID COLLECTION CONTAINERS

This application is a continuation of U.S. patent application Ser. No. 07/853/784 filed Mar. 19, 1992, now U.S. Pat. No. 5,267,987.

BACKGROUND OF THE INVENTION

It is frequently the case that incontinent individuals or persons with other medical problems require a portable device that can collect body fluids which can be worn on the users person, Unlike prior attempts to provide a system for collecting body fluids, this invention teaches a fastening system for body fluid collection containers which is worn around the user's leg, and that is lightweight, easy to put on, comfortable to wear, and easy to take off.

U.S. Pat. No. 4,511,358 to Johnson, Jr. et al. shows a urine bag carrier, but relies on a complicated and cumbersome system of belts to support the urine bag, unlike the present invention, which relies on a single support which wraps around the user's thigh.

U.S. Pat. No. 4,901,375 to Dahlgren shows a male urinal appliance, but differs from the present invention because Dahlgren is intended for use with bed ridden patients, whereas the present invention can be worn by an active person. Moreover, Dahlgren also relies on a complicated system of belts to support the urinal bottle.

U.S. Pat. No. 4,892,527 to Zivny shows a sportman's reusable, anti-collapsing urine collection device; however, Zivny is distinguishable from the present invention because it does not utilize a urine bag which is detachable from the bag support system.

U.S. Pat. No. 3,357,430 to Rosenberg also shows a urinary appliance, but differs from the present invention because in Rosenberg the system for supporting the reservoir is not adjustable to conform with the leg size of the user.

U.S. Pat. No. 4,073,295 to Laufbahn shows a catheter, but differs from the present invention, because Laufbahn does not teach a system whereby the urine bag can be easily detached from the bag support system and easily replaced without removing the bag support system.

BRIEF SUMMARY OF THE INVENTION

The preferred embodiment of the invention consists of a device which encircles the users leg, which is substantially in the shape of a rectangle having first and second ends, which the user wraps around the thigh portion of the user's leg. On each end of the bag support are fasteners, which coact with each other so that the first end of the bag support may be coupled with the second end. This frictionally secures the bag support to the users thigh. The bag support further has a bag attachment mechanism, which allows the urine bag to be affixed to the bag support. The bag attachment mechanism is configured so that the body fluid collection bag may be attached or detached as the user deems convenient. This allows the bag to be attached, removed after same becomes filled with a certain amount of fluid, emptied, and then reattached without forcing the user to remove the bag support.

It is the principle object of this invention to provide a comfortable, convenient and adjustable device for attaching and supporting a body fluid collection container to the thigh of a user.

It is also an object of this invention to provide a device that can support a body fluid collection container that can adjust to fit the legs of different persons.

It is an additional object of the invention to teach a device that allows the removal of a body fluid collection container without having to remove the body fluid container support system from the leg of the user.

It is another object of the invention to teach a device that can support a body fluid collection container under clothing.

It is a further object of the invention to teach a method of attaching and detaching a body fluid container to a body fluid container support.

Numerous other advantages and features of the invention will become readily apparent from the detailed description of the preferred embodiment of the invention, from the claims, and from the accompanying drawings, in which like numerals are employed to designate like parts throughout the same.

BRIEF DESCRIPTION OF THE DRAWINGS

A fuller understanding of the foregoing may be had by reference to the accompanying drawings, wherein:

FIG. 1 is a perspective view of the preferred embodiment of the present invention in the environment;

FIG. 2 is an exploded perspective view of the preferred embodiment of the invention of FIG. 1;

FIG. 3 is a front view of the body fluid container of the preferred embodiment of the invention of FIG. 1; and FIG. 4 is a front view of the leg encircling mechanism of the preferred embodiment of the invention of FIG. 1.

DESCRIPTION OF THE PREFERRED EMBODIMENT

While the invention is susceptible of embodiment in many different forms there is shown in the drawings and will be described herein in detail, preferred and alternate embodiments of the invention. It should be understood, however, that the present disclosure is to be considered an exemplification of the principles of the invention and is not intended to limit the spirit and scope of the invention and/or claims of the embodiments illustrated.

Referring now to the drawings, FIG. 1 shows the preferred embodiment of the present invention 10 disposed on human leg 25. The invention 10 has leg encircling mechanism 20, which is wrapped around users thigh 27, leg encircling mechanism 20 thereby supporting body fluid container 190. Body fluid container 190 has hose nozzle 200, which in turn has attached thereto collecting hose 207, the other end of collecting hose 207 attached to a fluid collection device (not shown).

FIG. 2 shows the preferred embodiment of the invention 10, showing leg encircling mechanism 20 and body fluid container 190. Leg encircling mechanism 20 has body fluid container support closure 110, and body fluid container attachment mechanism 150.

In the preferred embodiment of the invention 10, leg encircling mechanism 20 is constructed of a light, breathable yet sturdy cloth such as cotton, but could be made of other types of cloth, or any other type of flexible material such as elastic, plastic or nylon. The leg encircling mechanism 20 may, but need not, have attached thereto elastic strip 180, which joins first part 55 and second part 65, and allows the leg encircling mechanism 20 to flex while being worn by the user. Leg encircling mechanism 20 having first part 55 and second part 65, further has a first end 30, a second end 40, inside surface 50 and outside surface 60. Leg encircling mechanism 20 also has a first end upper corner 70, a first end lower corner 80, a second end upper corner 90, and a second end lower corner 100.

The body fluid container support closure 110 is disposed on first end 30 and second end 40 of leg encircling mechanism 20. The body fluid container support closure 110 consists of a first end fastener 130 and a second end fastener 140. The first end fastener 130 and the second end fastener 140 are so disposed on leg encircling mechanism 20 so that when leg encircling mechanism 20 is flexed to form a substantially cylindrical configuration as shown in FIG. 2, the first end fastener 130 may be aligned and coupled to second end fastener 140 of leg encircling mechanism 20.

In the preferred embodiment of the invention 10, the first end fastener 130 and the second end fastener 140 are hook and loop fasteners (which may be of VELCRO), which firmly couple the first end 30 of leg encircling mechanism 20 to the second end 40 of leg encircling mechanism 20. Because of the hook and loop fasteners, body fluid container support closure 110 is positionally adjustable, which allows the user to increase or decrease the diameter of the closed leg encircling mechanism 20. The invention 10 may therefore be used by different persons having legs of different sizes, or may be fitted onto different portions of a users thigh.

While the preferred embodiment of the invention uses hook and loop fasteners for the body fluid container support closure 110, other embodiments of the invention 10 could use different means of fastening the first end 30 to second end 40, so long as first end 30 and second end 40 may be reusably coupled and uncoupled. Other means of fastening include, but are not limited to, snaps, hooks, buttons, or zippers.

As illustrated in FIG. 2, the leg encircling mechanism 20 also has disposed thereon a body fluid container attachment mechanism 150. In the preferred embodiment of the invention 10, body fluid container attachment mechanism 150 consists of hook and loop fasteners 160, 165,170 and 175 disposed, respectively, on leg encircling mechanism 20 at the first end upper corner 70, first end lower corner 80, second end upper corner 90 and second end lower corner 100. Body fluid container attachment 150 in the preferred embodiment of the invention 10 further consists of hook and loop fasteners 260, 270, 280 and 290 on body fluid container 190 placed on first body fluid container corner 220, second body fluid container corner 230, third body fluid container corner 240, and fourth body fluid container corner 250. Hook and loop fasteners 260, 270, 280 and 290 on body fluid container 190 are positioned so that hook and loop fasteners 260, 270, 280, and 290 contact hook and loop fasteners 160, 165, 170 and 175, temporarily coupling body fluid container 190 to leg encircling mechanism 20. Body fluid container 190 further has hose nozzle 200, valve 205, and fluid reservoir 210.

While the preferred embodiment of the invention 10 uses hook and loop fasteners for body fluid container attachment mechanism 150, body fluid container attachment mechanism 150 can consist of any other type of fasteners to attach body fluid container 190 to leg encircling mechanism 20, including but not limited to snaps, hooks, buttons, or zippers, so long as said fasteners allow body fluid container 190 to be attached, removed, then reattached to leg encircling mechanism 20.

FIG. 3 shows body fluid container 190, which is a common urine bag of the disposable variety having body fluid container attachment mechanism 150 consisting of first body fluid container corner 220 with hook and loop fastener 260, second body fluid container corner 230 with hook and loop fastener 270, third body fluid container corner 240 with hook and loop fastener 280, and fourth body fluid container corner 250 with hook and loop fastener 290. Hook and loop fasteners 260, 270, 280 and 290 may be sewn onto body fluid container corners 220, 230, 240, and 250 or attached by any other method, such as with an adhesive. Body fluid container 190 further has hose nozzle 200, valve 205 and fluid reservoir 210. Hose nozzle 200 allows fluid to enter the body fluid container, filling fluid reservoir 210, and valve 205 allows fluid reservoir to be emptied when valve 205 is opened.

FIG. 4 shows leg encircling mechanism 20 of the preferred embodiment of the invention 10 having first end 30, second end 40, outside surface 60, first end upper corner 70, first end lower corner 80, second end upper corner 90, and second end lower corner 100. Leg encircling mechanism 20 also has first part 55 and second part 65. First part 55 and second part 65 are shown to be of substantially trapezoidal configuration. However, it is to be understood that these parts may be of any suitable configuration such as rectangular. Leg encircling mechanism 20 further has body fluid container support closure 110, consisting of first end fastener 130 and second end fastener 140. Also shown is body fluid container attachment mechanism 150, consisting of hook and loop fasteners 160, 165, 170 and 175 disposed on first end upper corner 70, first end lower corner 80, second end upper corner 90, and second end lower corner 100 respectively. Leg encircling mechanism 20 may, but need not, have elastic strips 180, which allows the leg encircling mechanism 20 to elastically expand during use, and to also expand for wear on different sized legs.

As seen in FIG. 1, to operate the invention 10, the user wraps leg encircling mechanism 20 around human leg 25, so that inner surface 50 of the leg encircling mechanism 20 comes into direct contact with the users thigh 27. The user then grasps first end fastener 130 and couples it to second end fastener 140, so that leg encircling mechanism 20 by means of friction is snugly wrapped around users thigh 27. The user then orients body fluid container 190 so that hook and loop fasteners 260, 270, 280 and 290 on body fluid container 190 align with hook and loop fasteners 160, 165, 170 and 175. The user then pushes body fluid container 190 gently toward the leg encircling mechanism 20 until the hook and loop fasteners 260, 270, 280 and 290 contact hook and loop fasteners 160, 165, 170 and 175, coupling body fluid container 190 to leg encircling mechanism 20. The body fluid container 190 is thus firmly affixed to the user as illustrated in FIG. 1. The user may then attach collecting hose 207, which collects the body fluid, to hose nozzle 200, and the user may dress normally and thereafter engage in normal day to day activity.

After the fluid reservoir 210 of body fluid container 190 becomes filled with fluid, the user may detaches collecting hose 207 from hose nozzle 200 and may then detach the body fluid container 190 from leg encircling mechanism 20 by simply pulling on body fluid container 190 with enough force to disengage hook and loop fasteners 260, 270, 280 and 290 on body fluid container 190 from hook and loop fasteners 160, 165, 170 and 175 on leg encircling mechanism 20. The body fluid container 190 may then be emptied, sanitized and replaced on the leg encircling mechanism 20, or replaced with a new body fluid container of similar configuration to body fluid container 190. The above procedure is appropriately modified if body fluid container support closure 110 consists of snaps, hooks, buttons, or zippers, or some other fastener, or if the body fluid container attachment mechanism 150 consists of snaps, hooks, buttons, or zippers, or some other method.

The foregoing specification describes only the preferred embodiment and the alternate embodiment of the invention as shown. Other embodiments may be articulated as well. The terms and expressions therefore serve only to describe the invention by example only and not to limit the invention. It is expected that others will perceive differences which while differing from the foregoing, do not depart from the spirit and scope of the invention herein described and claimed.

I claim:

1. A system for fastening a body waste fluid container having a top and bottom portion to a human leg, said system comprising:
    a broad strap for completely encircling the human leg having first and second ends and top and bottom edges, said first and second ends having complimentary fasteners which coact and couple said first end to said second end in an overlapping fashion, said broad strap being frictionally and detachably securable to the human leg;
    a body fluid container having a top and bottom portion and defining a length and having a body fluid collection means at said top portion and a body fluid release means at said bottom portion; and
    means for removably attaching solely said top and bottom portions of said body fluid container directly to said broad strap at said top and bottom edge thereof.

2. The invention of claim 1, wherein said broad strap has a first part and a second part.

3. The invention of claim 2, wherein said first and second parts of said broad strap are connected completely therebetween by a stretchable material to form a continuous broad strap.

4. The device of claim 3, wherein said broad strap is of substantially a trapezoidal configuration when lying flat.

5. The device of claim 1, wherein said means for fastening is hook and loop type fasteners.

6. The device of claim 1, wherein said means for removably attaching is hook and loop type fasteners.

* * * * *